United States Patent [19]
Brown

[11] Patent Number: 5,722,976
[45] Date of Patent: Mar. 3, 1998

[54] APPARATUS AND METHOD FOR SURGICALLY SECURING BONE PARTS

[76] Inventor: Robin Peter Brown, 4 Fraser Street, Middle Park, Victoria 3206, Australia

[21] Appl. No.: 600,925
[22] PCT Filed: Aug. 29, 1994
[86] PCT No.: PCT/AU94/00504
  § 371 Date: Jun. 26, 1996
  § 102(e) Date: Jun. 26, 1996
[87] PCT Pub. No.: WO95/05782
  PCT Pub. Date: Mar. 2, 1995

[30] Foreign Application Priority Data

Aug. 27, 1993 [AU] Australia ................ PM 0901

[51] Int. Cl.$^6$ ........................................ A61B 17/58
[52] U.S. Cl. .................. 606/69; 606/70; 606/71; 606/60; 606/72; 606/73
[58] Field of Search ................ 606/69, 70, 71, 606/60, 61, 72, 75

[56] References Cited

U.S. PATENT DOCUMENTS 4,802,477  2/1989  Gabbay ................ 128/317

FOREIGN PATENT DOCUMENTS

| 0718097 | 2/1980 | U.S.S.R. | 606/71 |
| 0862937 | 9/1981 | U.S.S.R. | 606/71 |
| 1405091 | 9/1975 | United Kingdom | 606/71 |

*Primary Examiner*—Michael Buiz
*Assistant Examiner*—Daphja Shai
*Attorney, Agent, or Firm*—Kerkam, Stowell, Kondracki & Clarke, P.C.; John C. Kerins

[57] ABSTRACT

An apparatus and method are provided for surgically securing bone parts, in particular for transsternal bilateral thoracotomy. The apparatus comprises a base piece from which are protruding two posts welded or attached thereto which are internally screwthreaded and adapted to receive screws, and a plate with holes is adapted to be positioned over the posts and secured relative to them by the screws. In the method of securing the bone parts using the apparatus, the posts are inserted into holes drilled in each respective bone part, so that the bone parts are held together with their sawn surfaces mutually opposing, and the plate is positioned above the bone parts and screwed into position into the posts by the screws through the holes and the plate.

17 Claims, 1 Drawing Sheet

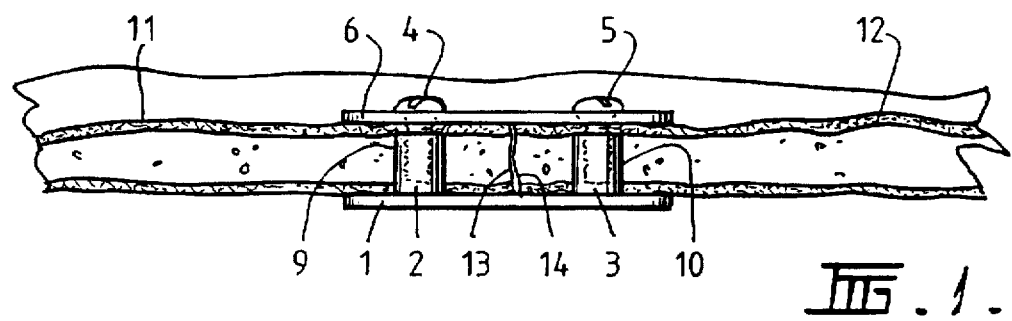
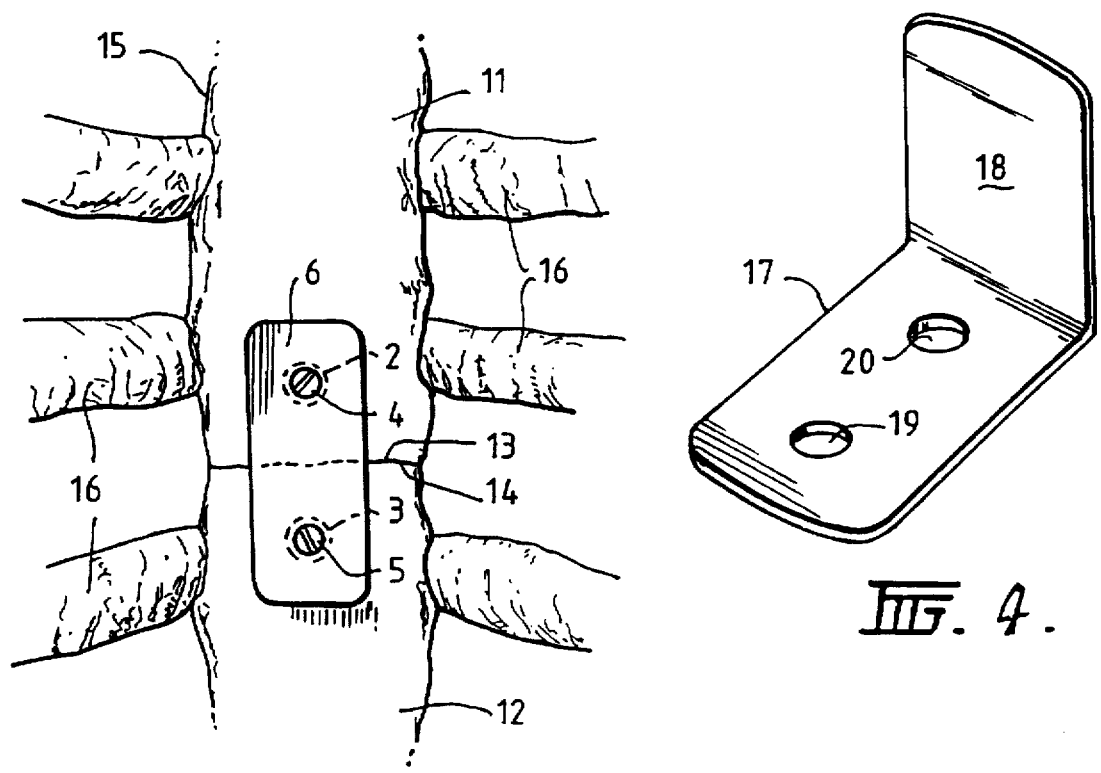
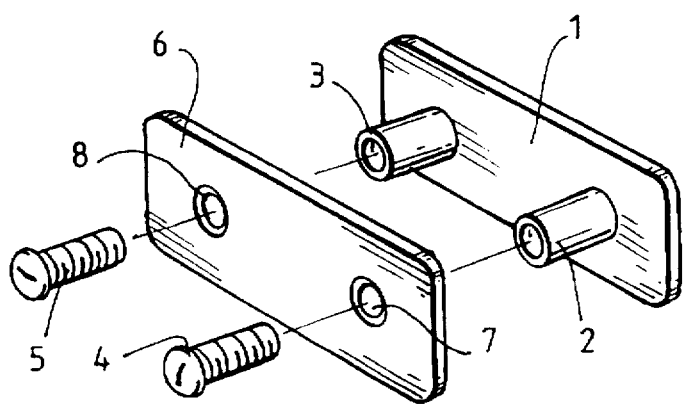

APPARATUS AND METHOD FOR SURGICALLY SECURING BONE PARTS

This invention relates to a method and apparatus for surgically securing bone parts, and in particular but not limited to surgery in humans where the sternum is desired to be re-joined after being sawn into two parts transversely.

In cardiothoracic surgery, a trans-sternal bilateral thoracotomy is often performed in order to gain access to the heart and/or lungs. In this procedure, the sternum is sawn into two pieces laterally. A particular problem arises with this procedure in providing a secure closure of the sternum at the end of the operation. The conventional technique is to secure the sternum with two or three sutures of wire passed through the bone above and below. The two parts of the sternum are held together by the sutures, and the closure must be completely secure with no motion at the sternal incision if the bone is to heal properly. Currently, the failure rate of such sternal closures is on averages 30% and in some hospitals 60%. It is thought that factors which influence the high failure rate include the fragility of the sternum and the small cross-sectional area of the transverse sternum closure. The problem does not arise in alternative means of opening the sternum where the sternum is cut longitudinally, presumably because the longitudinal incision has a much larger cross-sectional area.

The object of the invention is to provide an alternative apparatus and method for securing bone parts, and in particular to provide an apparatus and method for closing transverse sternum incisions which provides a higher reliability than conventional methods.

Therefore in accordance with a first broad aspect of the invention there is provided an apparatus for surgically securing a first bone part to a second bone part, comprising a base and first and second securing means for attaching to the base and for securing each respective bone part to the base firmly such that relative movement of the bone parts is prevented and re-growth of the bone parts into an integral whole is promoted, each securing means preventing movement or relative pivoting of the corresponding bone part outwards from the base by holding the corresponding bone part onto the base, wherein (i) the holding is performed by the application of external pressure applied to the bone parts by the securing means on a side of the bone parts opposite to the base; and (ii) one or both of said securing means comprises a screw means and a receiving means, said screw means in use being inserted from one side through a drilled hole in the corresponding bone part and screwed into the receiving means disposed on the other said side of the bone; and (iii) one or both of said securing means includes a post protruding from the base over which in use the corresponding bone part is positioned with the post inside the drilled hole.

For each said securing means, a plurality of screw means and receiving means and corresponding drilled holes may be provided.

Preferably, the or each receiving means comprises said post and in use the screw means is screwed into a thread in the post from a side of the corresponding bone part opposite the base.

The post may be welded, moulded or otherwise integrally formed with the base, or alternatively may be detachably joined to the base by attachment screws.

Still preferably, the apparatus and securing means further comprise a plate with a first hole and a second hole adapted to be positioned under heads on the screw means associated with the first and second securing means respectively, the plate being held in position on the bone part by the screw means and thereby providing said holding.

Alternatively, an enlarged head or washer on the or each screw means may act to provide said holding.

The apparatus can be made from any physiologically acceptable material capable of withstanding the stresses placed on it during use.

Preferably the apparatus is made from stainless steel or titanium to allow the provision of a thin base and a securing means which protrude as little as possible from the bone surface. The apparatus can also be constructed from a bioabsorbable material, thereby avoiding any future need to remove the apparatus.

Optionally, the base and/or plate are perforated to allow bone growth between the perforations. The perforations may be realised by constructing the base and/or plate from porous material.

According to a second broad aspect of the invention there is provided a method of surgically securing a first bone part to a second bone part, comprising making holes in each bone part, positioning the first bone part over a post protruding from a base, positioning the second bone part over a second post protruding from the base, said holes being made in appropriate positions in the corresponding bone parts so that the bone parts are held through their holes on the respective posts and sawn surfaces of the corresponding bone parts are mutually opposed and held together, attaching holding means to the posts so as to provide securing means which prevent movement of each corresponding bone part outwards from the base by holding the corresponding bone part onto the base with external pressure on the corresponding bone part.

Preferably in the case of a bone which is sawn into the two bone parts during an operation, the holes are drilled before the bone is sawn.

In order that the invention can be more clearly ascertained, a preferred embodiment will now be described with reference to the accompanying drawings, in which:

FIG. 1 is a side cross-sectional view of the apparatus of the preferred embodiment installed and holding two bone parts together;

FIG. 2 is a view of the apparatus of the preferred embodiment installed on a sternum closure;

FIG. 3 shows individual parts of the apparatus of the preferred embodiment; and

FIG. 4 shows a template for use in performing a preferred method.

Now referring to FIG. 3, there is shown a metal base 1 from which are protruding two posts 2 and 3 welded thereto which are internally screw threaded and adapted to receive screws 4 and 5. Optionally, the posts may be detachable from the base by screws or other means in order to facilitate the provision of varied post lengths to accommodate varied sternal thickness. A plate 6 with holes 7 and 8 is adapted to be positioned over the posts 2 and 3 and secured relative to them by the screws 4 and 5.

Referring now to FIG. 1, it can be seen that the posts 2 and 3 are inserted into holes 9 and 10 drilled in each respective bone part 11 and 12, so that the bone parts are held together with their sawn surfaces 13 and 14 mutually opposing. The plate 6 is positioned above the bone parts and screwed into position into the posts by the screws 4 and 5 through the holes in the plate 7 and 8. It can be seen from FIG. 1 that the securing means referred to in the first broad aspect of the invention may be provided by the combination of post 2 screw 4 and plate 6 in the case of the first securing means and the combination of post 3 screw 5 and plate 6 in the case of the second securing means.

FIG. 1 shows a gap between the top of the post and the plate. This is not necessary and if the post length is measured exactly may be eliminated to provide a more secure fixation.

Referring now to FIG. 2, a view of the sternum closure can be seen from above showing the sternum 15 and the incision which produces the sawn faces 13 and 14 of the two sternum parts 11 and 12. The ribs of the patient 16 extend laterally from the sternum. The plate 6 can be seen held into place by the screws 4 and 5.

It has been found that the apparatus as described above provides a superior sternum closure of greater security than the conventional wire method of closure, reliably preventing relative movement of the bone parts 11 and 12 and thereby promoting healing of the bone.

Referring now to FIG. 4, in the preferred method provided by the invention as described above, drilling of the holes in each bone part can be facilitated by the provision of a template 17 with holes 19 and 20 which are positioned to correspond with the holes 7 and 8 of the plate 6. Before the sternum is sawed the template is positioned appropriately on the sternum with the aid of the handle 18. The drilling through holes in the template 19 and 20 is then easily performed. The incision is then made between the holes, preferably near the middle. At the end of the operation the first bone part 12 is positioned above the first post 3 on the base 1. The second bone part 11 is then lowered onto the post 2. Thereafter all procedures can be carried out above the sternum, which comprise simply placing the plate 6 over the holes and securing the screw means 4 and 5 into the posts 2 and 3.

Further modifications made to the invention as would be apparent to persons skilled in surgery. These and other modifications may be made without departing from the ambit of the invention the nature of which is to be determined from the foregoing description, the claims and the drawings.

I claim:

1. An apparatus for surgically securing a first bone part to a second bone part, comprising a base and first and second securing means for attaching to the base and for securing each respective bone part to the base firmly such that relative movement of the bone parts is prevented and re-growth of the bone parts into an integral whole is promoted, each securing means preventing movement or relative pivoting of the corresponding bone part outwards from the base by holding the corresponding bone part onto the base wherein (i) the holding is performed by the application of external pressure applied to the bone parts by said first and second securing means on a side of the bone parts opposite to the base; and (ii) said first securing means comprises a first screw means and a receiving means, said first screw means in use being inserted from a first outer bone surface through a first drilled hole in a first corresponding bone part and screwed into the receiving means disposed at an opposing outer surface of the bone part;

(iii) said first securing means includes a first post protruding from the base over which, in use, the first corresponding bone part is positioned with the first post inside the first drilled hole; and wherein said second securing means comprises a second screw means and a receiving means, said second screw means in use being inserted from a first outer bone surface through a second drilled hole in a second corresponding bone part and screwed into the receiving means disposed at an opposing outer surface of the second bone part; and said second securing means includes a second post protruding from the base over which, in use, the second corresponding bone part is positioned with said second post inside the second drilled hole.

2. An apparatus as claimed in claim 1 wherein said receiving means of said first securing means comprises said first post and, in use, the first screw means is screwed into a thread in the first post from a side of the corresponding bone part opposite the base.

3. An apparatus as claimed in claim 2 wherein said first post is welded, molded or otherwise integrally formed with the base.

4. An apparatus as claimed in claim 2 wherein said first post is detachably joined to the base by attachment screws.

5. An apparatus as claimed in claim 4 wherein said securing means further comprises an enlarged head or washer for installation under said first screw means and wherein said enlarged head or washer provides said holding.

6. An apparatus as claimed in claim 1, wherein said securing means further comprises a plate with a first hole and a second hole spaced apart at a distance adapted to receive said first and second screw means therethrough, and to be retained by said first and second screw means on a side of said bone part opposite said base, and at a predetermined distance from said base, thereby providing said holdings.

7. An apparatus as claimed in claim 6 wherein at least one of said base and plate is perforated to allow bone growth in the perforations.

8. An apparatus as claimed in claim 6 wherein at least one of said base and plate is made from bioabsorbable material.

9. An apparatus as claimed in claim 8 adapted for closing transverse sternum incisions.

10. An apparatus as claimed in claim 6 wherein both said base and said plate are perforated to allow bone growth in the perforations.

11. An apparatus as claimed in claim 6 wherein both said base and said plate are made from bioabsorbable material.

12. An apparatus as claimed in claim 1 wherein said receiving means of said second securing means comprises said second post and, in use, the second screw means is screwed into a thread in the second post from a side of the corresponding bone part opposite the base.

13. An apparatus as claimed in claim 1 wherein said second post is welded, molded or otherwise integrally formed with the base.

14. An apparatus as claimed in claim 1 wherein said second post is detachably joined to the base by attachment screws.

15. An apparatus as claimed in claim 1 wherein said securing means further comprises an enlarged head or washer for installation under said second screw means wherein said enlarged head or washer provides said holding.

16. A method of surgically securing a first bone part to a second bone part, comprising making holes in each bone part, positioning the first bone part over a post protruding from a base, positioning the second bone part over a second post protruding from the base, said holes being made in appropriate positions in the corresponding bone parts so that the bone parts are held through their holes on the respective posts and predetermined surfaces of the corresponding bone parts are mutually opposed and held together, attaching holding means to the posts so as to provide securing means which prevent movement of each corresponding bone part outwards from the base by holding the corresponding bone part onto the base with external pressure on the corresponding bone part.

17. A method as claimed in claim 16 wherein the bone is sawn into said bone parts during an operation and said holes are drilled before the bone is sawn.

* * * * *